United States Patent
Ishihara et al.

(10) Patent No.: US 11,383,226 B2
(45) Date of Patent: Jul. 12, 2022

(54) CATALYST FOR ORGANIC SUBSTANCE DECOMPOSITION AND ORGANIC SUBSTANCE DECOMPOSING APPARATUS

(71) Applicant: Murata Manufacturing Co., Ltd., Nagaokakyo (JP)

(72) Inventors: Kentaro Ishihara, Nagaokakyo (JP); Nario Sugahara, Nagaokakyo (JP); Satoshi Kuretake, Nagaokakyo (JP); Naoya Mori, Nagaokakyo (JP); Hideto Sato, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 181 days.

(21) Appl. No.: 17/018,666

(22) Filed: Sep. 11, 2020

(65) Prior Publication Data
US 2020/0406236 A1 Dec. 31, 2020

Related U.S. Application Data

(63) Continuation of application No. PCT/JP2019/017674, filed on Apr. 25, 2019.

(30) Foreign Application Priority Data

May 11, 2018 (JP) .............................. JP2018-092386

(51) Int. Cl.
*B01D 53/94* (2006.01)
*B01J 23/34* (2006.01)
(Continued)

(52) U.S. Cl.
CPC ............. *B01J 23/8892* (2013.01); *A61L 9/03* (2013.01); *B01D 53/865* (2013.01);
(Continued)

(58) Field of Classification Search
None
See application file for complete search history.

(56) References Cited

U.S. PATENT DOCUMENTS

| 8,329,612 B2 | 12/2012 | Sato et al. |
| 2002/0035035 A1 | 3/2002 | Kirchnerova et al. |
| | (Continued) | |

FOREIGN PATENT DOCUMENTS

| JP | H0780310 A | 3/1995 |
| JP | 2000140635 A | 5/2000 |
| | (Continued) | |

OTHER PUBLICATIONS

Liu et al., Controlled preparation and high catalytic performance of three-dimensionally ordered microporous LaMnO3 with nanovoid skeletons for the combustion of toluene, Journal of Catalysis, 2012, 287, 149-160 (Liu). (Year: 2012).*

(Continued)

*Primary Examiner* — Melissa S Swain
*Assistant Examiner* — Keling Zhang
(74) *Attorney, Agent, or Firm* — ArentFox Schiff LLP (57) ABSTRACT

A catalyst for decomposing an organic substance, the catalyst having a body which has a plurality of pores and the body contains a perovskite-type composite oxide represented by $A_xB_yM_zO_w$, where the A contains at least one selected from Ba and Sr, the B contains Zr, the M is at least one selected from Mn, Co, Ni, and Fe, $1.001 \leq x \leq 1.1$, $0.05 \leq z \leq 0.2$, $y+z=1$, and w is a positive value that satisfies electrical neutrality. The average pore diameter of the plurality of pores is 49 nm to 260 nm and the pore volume of each of the plurality of pores is 0.08 cm³/g to 0.37 cm³/g.

10 Claims, 2 Drawing Sheets

(51) Int. Cl.

| | | |
|---|---|---|
| *B01J 23/889* | (2006.01) | |
| *A61L 9/03* | (2006.01) | |
| *B01D 53/86* | (2006.01) | |
| *B01J 23/00* | (2006.01) | |
| *B01J 23/68* | (2006.01) | |
| *B01J 23/78* | (2006.01) | |
| *B01J 35/10* | (2006.01) | |
| *C01G 45/12* | (2006.01) | |
| *C01G 51/00* | (2006.01) | |
| *C01G 53/00* | (2006.01) | |
| *B01J 21/06* | (2006.01) | |
| *B01J 35/04* | (2006.01) | |
| *B01J 21/04* | (2006.01) | |
| *B01J 35/02* | (2006.01) | |
| *B01J 37/00* | (2006.01) | |
| *B01J 21/16* | (2006.01) | |

(52) U.S. Cl.
CPC ..... *B01D 53/8668* (2013.01); *B01D 53/8687* (2013.01); *B01D 53/8696* (2013.01); *B01D 53/94* (2013.01); *B01J 21/04* (2013.01); *B01J 21/066* (2013.01); *B01J 23/002* (2013.01); *B01J 23/34* (2013.01); *B01J 23/688* (2013.01); *B01J 23/78* (2013.01); *B01J 35/026* (2013.01); *B01J 35/04* (2013.01); *B01J 35/1009* (2013.01); *B01J 35/1038* (2013.01); *B01J 35/1061* (2013.01); *B01J 35/1066* (2013.01); *B01J 35/1071* (2013.01); *B01J 35/1076* (2013.01); *C01G 45/125* (2013.01); *C01G 45/1207* (2013.01); *C01G 51/66* (2013.01); *C01G 53/66* (2013.01); *B01D 2255/104* (2013.01); *B01D 2255/2042* (2013.01); *B01D 2255/2047* (2013.01); *B01D 2255/2061* (2013.01); *B01D 2255/2063* (2013.01); *B01D 2255/2073* (2013.01); *B01D 2255/2092* (2013.01); *B01D 2255/2094* (2013.01); *B01D 2255/20707* (2013.01); *B01D 2255/20715* (2013.01); *B01D 2255/20738* (2013.01); *B01D 2255/20746* (2013.01); *B01D 2255/20753* (2013.01); *B01D 2255/20792* (2013.01); *B01D 2255/402* (2013.01); *B01D 2255/9202* (2013.01); *B01D 2255/9207* (2013.01); *B01D 2257/7027* (2013.01); *B01D 2258/01* (2013.01); *B01D 2258/02* (2013.01); *B01J 21/16* (2013.01); *B01J 37/009* (2013.01); *C01P 2002/34* (2013.01); *C01P 2002/50* (2013.01); *C01P 2002/72* (2013.01); *C01P 2002/77* (2013.01); *C01P 2006/12* (2013.01); *C01P 2006/14* (2013.01); *C01P 2006/16* (2013.01)

(56) References Cited

U.S. PATENT DOCUMENTS

| | | |
|---|---|---|
| 2007/0627031 | 2/2007 | Ikeda et al. |
| 2007/0249497 A1 | 10/2007 | Tanaka et al. |
| 2009/0131252 A1 | 5/2009 | Tanaka et al. |
| 2009/0286677 A1 | 11/2009 | Takeshima et al. |
| 2012/0074357 A1 | 3/2012 | Sato et al. |
| 2016/0115835 A1 | 4/2016 | Daido et al. |

FOREIGN PATENT DOCUMENTS

| | | |
|---|---|---|
| JP | 3406001 B2 | 5/2003 |
| JP | 2006231280 A | 9/2006 |
| JP | 2006346603 A | 12/2006 |
| JP | 2006347825 A | 12/2006 |
| JP | 5076377 B2 | 11/2012 |
| JP | 2013244479 A | 12/2013 |
| JP | 2015229137 A | 12/2015 |
| JP | 6036276 B2 | 11/2016 |
| WO | 0016900 A1 | 3/2000 |
| WO | 2004096436 A1 | 11/2004 |
| WO | 2065058490 A1 | 6/2005 |
| WO | 2010143676 A1 | 12/2010 |
| WO | 2014189115 A1 | 11/2014 |
| WO | 2015194451 A1 | 12/2015 |

OTHER PUBLICATIONS

Japanese Office Action issued for Japanese Application No. 2020-518162, dated Jun. 29, 2021.
International Search Report issued for PCT/JP2018/045261, dated Feb. 5, 2019.
Kirchenerova, J. et al.; "Design criteria for high-temperature combustion catalysts"; Catalysis Letters, Jul. 2000, vol. 67, No. 2-4, pp. 175-181.
International Search Report issued for PCT/JP2019/017674, dated Jul. 16, 2019.
International Search Report issued for PCT/JP2019/015483, dated Jul. 16, 2019.
International Search Report issued for PCT/JP2019/008692, dated May 21, 2019.
International Search Report issued for PCT/JP2019/008593, dated May 21, 2019.
Written Opinion of the International Searching Authority issued for PCT/JP2019/008593, dated May 21, 2019.
Written Opinion of the International Searching Authority issued for PCT/JP2019/008592, dated May 21, 2019.
Written Opinion of the International Searching Authority issued for PCT/JP2019/015483, dated Jul. 16, 2019.
Written Opinion of the International Searching Authority issued for PCT/JP2019/017674, dated Jul. 16, 2019.
Written Opinion of the International Searching Authority issued for PCT/JP2018/045261, dated Feb. 5, 2019.
Gallucci, Katia et al.; "Catalytic combustion of methane on BaZr$_{(1-x)}$Me$_x$O$_3$ perovskites synthesized by a modified citrate method"; Catalysis Today, 2012, vol. 197, No. 1, pp. 236-242.
Tuyen, Nguyen Van et al.; "Interaction of Hydrogen with Perovskite-supported Metal Catalysts: I. M/Sr$_{1-x}$Zr$_{1-y}$O$_{3-\alpha}$ (M=Cu, Pd)"; Kinetics and Catalysis, 1996, vol. 37, No. 4, pp. 575-578.

* cited by examiner

CATALYST FOR ORGANIC SUBSTANCE DECOMPOSITION AND ORGANIC SUBSTANCE DECOMPOSING APPARATUS

CROSS REFERENCE TO RELATED APPLICATIONS

The present application is a continuation of International application No. PCT/JP2019/017674, filed Apr. 25, 2019, which claims priority to Japanese Patent Application No. 2018-092386, filed May 11, 2018, the entire contents of each of which are incorporated herein by reference.

FIELD OF THE INVENTION

The present invention relates to a catalyst for decomposing an organic substance and an organic substance decomposing apparatus which includes a catalyst for decomposing an organic substance.

BACKGROUND OF THE INVENTION

Conventionally, catalysts for decomposing organic substances have been known. Such catalysts are used at high temperatures in some cases, and it is thus preferable that the catalytic activity hardly decreases even when the catalysts are exposed to high temperatures.

Patent Document 1 describes a catalyst for decomposing an organic substance which contains a perovskite-type composite oxide represented by a general formula $ABO_3$, where the A site contains Ba, the B site contains Zr, and a part of the Zr is substituted with at least one of Mn, Co, or Ni. It is said that this catalyst for decomposing an organic substance does not contain a noble metal and can suppress a decrease in its catalytic activity even when being subjected to a heat treatment at 800° C. for 100 hours.

Patent Document 2 describes a catalyst for exhaust gas purification including a porous silica carrier having a pore structure and particles of a perovskite-type composite oxide supported in the pore structure of the porous silica carrier. This catalyst for exhaust gas purification is said to exhibit excellent performance in catalytic activity at relatively high temperatures by being configured so that the peak attributed to the gap between the primary particles of silica is in a range of 5 to 50 nm and a peak attributed to the pore structure of silica is in a range of 1 to 5 nm in the pore distribution of the porous silica carrier.

Patent Document 3 describes a catalyst for exhaust gas purification which has a structure in which an oxide represented by a general formula $La_xM_{(1-x)}M'O_{3-\delta}$ is supported on an oxide exhibiting oxygen absorbing and releasing ability and in which the diameters of pores having a pore volume proportion of 90 vol % are 150 nm or less and the average pore diameter is 15 nm to 36 nm in the cumulative pore volume distribution. Patent Document 3 describes that this catalyst for exhaust gas purification exhibits superior purification performance to conventional catalysts for exhaust gas purification.

Patent Document 1: Japanese Patent No. 6303834
Patent Document 2: Japanese Patent No. 5076377
Patent Document 3: Japanese Patent No. 6036276

SUMMARY OF THE INVENTION

It is said that the catalyst for decomposing an organic substance described in Patent Document 1 can suppress a decrease in its catalytic activity even when being subjected to a heat treatment at 800° C. for 100 hours, but it is desired that a decrease in catalytic activity can be suppressed even when a catalyst is exposed to a temperature higher than 800° C. The inventors have attempted to apply the pore diameter described in Patent Documents 2 and 3 to the catalyst for decomposing an organic substance described in Patent Document 1, but have found that a decrease in catalyst activity cannot be sufficiently suppressed when the catalyst is exposed to a temperature higher than 800° C.

The present invention is intended to solve the above problems, and an object thereof is to provide a catalyst for decomposing organic substances which can suppress a decrease in its catalytic activity when being exposed to a temperature higher than 800° C. and an organic substance decomposing apparatus which includes such a catalyst.

The catalyst for decomposing organic substances of the present invention is a catalyst comprising a body having a plurality of pores, the body containing a perovskite-type composite oxide represented by $A_xB_yM_zO_w$, where the A contains at least one selected from Ba and Sr, the B contains Zr, the M is at least one selected from Mn, Co, Ni, and Fe, $1.001 \leq x \leq 1.1$, $0.05 \leq z \leq 0.2$, $y+z=1$, w is a positive value that satisfies electrical neutrality, and an average pore diameter of the plurality of pores is 49 nm to 260 nm and a pore volume of each of the plurality of pores is 0.08 $cm^3/g$ to 0.37 $cm^3/g$.

The organic substance decomposition rate after the catalyst is subjected to a heat treatment at 1400° C. for 3 hours may be greater than 0.97 when the organic substance decomposition rate before the heat treatment is regarded as 1.

The x may satisfy a relation of $1.001 \leq x \leq 1.05$.

The pore volume may be 0.10 $cm^3/g$ to 0.37 $cm^3/g$.

The average pore diameter may be 150 nm to 260 nm, and the pore volume may be 0.21 $cm^3/g$ to 0.37 $cm^3/g$.

The organic substance decomposing apparatus of the present invention includes any catalyst for decomposing an organic substance described above.

According to the catalyst for decomposing an organic substance of the present invention, it is possible to suppress a decrease in catalytic activity when the catalyst is exposed to a temperature higher than 800° C.

The organic substance decomposing apparatus of the present invention can decompose an organic substance at a high decomposition rate even after the catalyst is exposed to a high temperature since the apparatus includes a catalyst for decomposing an organic substance which can suppress a decrease in its catalytic activity when being exposed to a temperature higher than 800° C.

DETAILED DESCRIPTION OF THE INVENTION

Hereinafter, the features of the present invention will be specifically described with reference to the embodiments of the present invention.

The catalyst for decomposing an organic substance according to the present invention satisfies the following requirements (hereinafter referred to as requirements of the present invention). In other words, the catalyst for decomposing an organic substance according to the present invention has a plurality of pores, and in which the catalyst contains a perovskite-type composite oxide represented by $A_xB_yM_zO_w$, where the A contains at least one selected from the group consisting of Ba and Sr, the B contains Zr, the M is at least one selected from the group consisting of Mn, Co, Ni, and Fe, $1.001 \leq x \leq 1.1$, $0.05 \leq z \leq 0.2$, $y+z=1$, w is a positive value that satisfies electrical neutrality, and an average pore diameter of the plurality of pores is 49 nm to 260 nm and a pore volume of each of the pores is 0.08 cm$^3$/g to 0.37 cm$^3$/g.

The catalyst for decomposing an organic substance which satisfies the requirements of the present invention can suppress a decrease in its catalytic activity when being exposed to a temperature higher than 800° C. as described later. This catalyst for decomposing an organic substance can be used in various applications to decompose organic substances such as purification of exhaust gas from factories and motor vehicles. In that case, it is possible to configure an organic substance decomposing apparatus including a catalyst for decomposing an organic substance which satisfies the requirements of the present invention.

Example 1

Powders of high-purity BaCO$_3$, ZrO$_2$, and MnCO$_3$ were weighed so as to have the composition presented in Table 1, pure water was added thereto, and the mixture was wet-mixed together with ZrO$_2$ cobble stones to obtain a slurry. This slurry was dried at 120° C. in a dryer, and the obtained powder was then subjected to a heat treatment at 1100° C. for 2 hours to obtain the intended perovskite-type composite oxide.

An additive and water were added to the obtained perovskite-type composite oxide, and the mixture was wet-mixed together with ZrO$_2$ cobble stones to obtain a slurry. In this slurry, the average particle diameter D50 of the perovskite-type composite oxide is 0.780 μm. This slurry was dried at 120° C. in a dryer and then molded using a press molding machine so as to be a cylindrical pellet having a molding density of 2.9 g/cm$^3$, a diameter of 8 mm, and a length of 8 mm. The obtained molded body was fired at 1050° C. for 2 hours to obtain a catalyst for decomposing an organic substance of Sample No. 2 in Table 1.

The catalysts for decomposing an organic substance of Sample Nos. 3 to 5 were respectively fabricated by the same method as that for the catalyst for decomposing an organic substance of Sample No. 2 except that the molding densities were different from one another as presented in Table 1.

The catalyst for decomposing an organic substance of Sample No. 6 was fabricated by the same method as that for the catalyst for decomposing an organic substance of Sample No. 2 except that the molding density was set to 2.6 g/cm$^3$ and firing was performed at 1450° C. for the purpose of setting the average pore diameter to be larger and the pore volume to be smaller than those of the catalyst for decomposing an organic substance of Sample No. 5 having the same molding density.

The catalyst for decomposing an organic substance of Sample No. 7 was fabricated by the same method as that for the catalyst for decomposing an organic substance of Sample No. 2 except that the molding density was set to 2.6 g/cm$^3$ and firing was performed at 1500° C. for the purpose of setting the average pore diameter to be larger and the pore volume to be smaller than those of the catalyst for decomposing an organic substance of Sample No. 6 having the same molding density.

The catalysts for organic substance decomposition of Sample Nos. 8 to 12 were fabricated by the same method as that for the catalyst for decomposing an organic substance of Sample No. 2 except that the molding densities were different from one another as presented in Table 1.

The catalyst for decomposing an organic substance of Sample No. 13 was fabricated by the same method as that for the catalyst for decomposing an organic substance of Sample No. 2 except that the molding density was set to 2.1 g/cm$^3$ and firing was performed at 1450° C. for the purpose of setting the average pore diameter to be larger and the pore volume to be smaller than those of the catalyst for decomposing an organic substance of Sample No. 12 having the same molding density.

The catalyst for decomposing an organic substance of Sample No. 14 was fabricated by the same method as that for the catalyst for decomposing an organic substance of Sample No. 2 except that the molding density was set to 2.1 g/cm$^3$ and firing was performed at 1500° C. for the purpose of setting the average pore diameter to be larger and the pore volume to be smaller than those of the catalyst for decomposing an organic substance of Sample No. 13 having the same molding density.

The catalyst for decomposing an organic substance of Sample No. 15 was fabricated by the following method. A perovskite-type composite oxide was obtained by the same method as the method for fabricating the catalyst for decomposing an organic substance of Sample No. 2, then an additive and water were added to the perovskite-type composite oxide, and the mixture was wet-mixed and dehydrated until to be clay-like for the purpose of increasing the average pore diameter and the pore volume. After that, the clay-like sample was hollowed out, dried again, and then molded using a press molding machine so as to be a cylindrical pellet having a molding density of 2.0 g/cm$^3$, a diameter of 8 mm, and a length of 8 mm. The obtained molded body was fired at 1050° C. for 2 hours to obtain a catalyst for decomposing an organic substance of Sample No. 15.

The catalyst for decomposing an organic substance of Sample No. 1 was fabricated by the following method. A perovskite-type composite oxide was obtained by the same method as the method for fabricating the catalyst for decomposing an organic substance of Sample No. 2, and then wet mixing was performed until the average particle diameter D50 became 0.563 μm for the purpose of decreasing the average pore diameter to obtain a slurry. This slurry was dried at 120° C. in a dryer and then molded using a press molding machine so as to be a cylindrical pellet having a molding density of 3.0 g/cm$^3$, a diameter of 8 mm, and a length of 8 mm. The obtained molded body was fired at 1050° C. for 2 hours to obtain a catalyst for decomposing an organic substance of Sample No. 1.

The catalyst for decomposing an organic substance of Sample No. 16 was fabricated by the following method. A perovskite-type composite oxide was obtained by the same method as the method for fabricating the catalyst for decomposing an organic substance of Sample No. 2, then an additive and water were added to the perovskite-type composite oxide, and the mixture was wet-mixed and dehydrated until to be clay-like for the purpose of decreasing the average pore diameter. In wet mixing, the average particle diameter D50 of the slurry was adjusted to 0.563 μm. After that, the clay-like sample was hollowed out, dried again, and then molded using a press molding machine so as to be a cylindrical pellet having a molding density of 2.0 g/cm³, a diameter of 8 mm, and a length of 8 mm. The obtained molded body was fired at 1050° C. for 2 hours to obtain a catalyst for decomposing an organic substance of Sample No. 16.

130°, the mercury surface tension was 485 mN/m, and the measurement pressure range was 3.45 kPa to 414 MPa.

<Evaluation on Catalytic Activity>

A method for evaluating the activity of the catalyst for decomposing an organic substance will be described.

TABLE 1

| Sample No. | Charged composition ratio | | | | A(x) | | B(y) | M(z) | | | | Firing temperature | Average particle diameter D50 μm |
|---|---|---|---|---|---|---|---|---|---|---|---|---|---|
| | x | y | z | y+z | Ba | Sr | Zr | Mn | Co | Ni | Fe | | |
| 1* | 1.010 | 0.900 | 0.100 | 1.000 | 1.000 | | 1.000 | 1.000 | | | | 1050° C. | 0.563 |
| 2 | 1.010 | 0.900 | 0.100 | 1.000 | 1.000 | | 1.000 | 1.000 | | | | 1050° C. | 0.780 |
| 3 | 1.010 | 0.900 | 0.100 | 1.000 | 1.000 | | 1.000 | 1.000 | | | | 1050° C. | 0.780 |
| 4 | 1.010 | 0.900 | 0.100 | 1.000 | 1.000 | | 1.000 | 1.000 | | | | 1050° C. | 0.780 |
| 5 | 1.010 | 0.900 | 0.100 | 1.000 | 1.000 | | 1.000 | 1.000 | | | | 1050° C. | 0.780 |
| 6 | 1.010 | 0.900 | 0.100 | 1.000 | 1.000 | | 1.000 | 1.000 | | | | 1450° C. | 0.780 |
| 7 | 1.010 | 0.900 | 0.100 | 1.000 | 1.000 | | 1.000 | 1.000 | | | | 1500° C. | 0.780 |
| 8 | 1.010 | 0.900 | 0.100 | 1.000 | 1.000 | | 1.000 | 1.000 | | | | 1050° C. | 0.780 |
| 9 | 1.010 | 0.900 | 0.100 | 1.000 | 1.000 | | 1.000 | 1.000 | | | | 1050° C. | 0.780 |
| 10 | 1.010 | 0.900 | 0.100 | 1.000 | 1.000 | | 1.000 | 1.000 | | | | 1050° C. | 0.780 |
| 11 | 1.010 | 0.900 | 0.100 | 1.000 | 1.000 | | 1.000 | 1.000 | | | | 1050° C. | 0.780 |
| 12 | 1.010 | 0.900 | 0.100 | 1.000 | 1.000 | | 1.000 | 1.000 | | | | 1050° C. | 0.780 |
| 13 | 1.010 | 0.900 | 0.100 | 1.000 | 1.000 | | 1.000 | 1.000 | | | | 1450° C. | 0.780 |
| 14 | 1.010 | 0.900 | 0.100 | 1.000 | 1.000 | | 1.000 | 1.000 | | | | 1500° C. | 0.780 |
| 15 | 1.010 | 0.900 | 0.100 | 1.000 | 1.000 | | 1.000 | 1.000 | | | | 1050° C. | 0.780 |
| 16* | 1.010 | 0.900 | 0.100 | 1.000 | 1.000 | | 1.000 | 1.000 | | | | 1050° C. | 0.563 |

| Sample No. | Molding density g/cm³ | Average pore diameter nm | Pore volume cm³/g | Before high temperature heat treatment Decomposition rate % | After high temperature heat treatment Decomposition rate % | Deterioration rate % |
|---|---|---|---|---|---|---|
| 1* | 3.0 | 32.1 | 0.13 | 92.6 | 85.5 | 7.6 |
| 2 | 2.9 | 49.4 | 0.15 | 94.0 | 91.5 | 2.7 |
| 3 | 2.8 | 66.6 | 0.17 | 94.6 | 93.3 | 1.4 |
| 4 | 2.7 | 83.9 | 0.19 | 95.3 | 94.3 | 1.1 |
| 5 | 2.6 | 101.1 | 0.21 | 96.0 | 95.1 | 0.9 |
| 6 | 2.6 | 152.0 | 0.14 | 92.5 | 92.1 | 0.4 |
| 7 | 2.6 | 170.0 | 0.08 | 89.1 | 88.9 | 0.2 |
| 8 | 2.5 | 118.4 | 0.23 | 96.7 | 95.9 | 0.8 |
| 9 | 2.4 | 135.6 | 0.25 | 97.4 | 96.7 | 0.7 |
| 10 | 2.3 | 152.9 | 0.27 | 98.1 | 97.5 | 0.6 |
| 11 | 2.2 | 170.1 | 0.30 | 98.8 | 98.2 | 0.6 |
| 12 | 2.1 | 187.4 | 0.33 | 99.5 | 98.9 | 0.6 |
| 13 | 2.1 | 240.0 | 0.24 | 97.2 | 96.9 | 0.3 |
| 14 | 2.1 | 260.0 | 0.21 | 94.9 | 94.8 | 0.1 |
| 15 | 2.0 | 204.6 | 0.37 | 99.9 | 99.4 | 0.5 |
| 16* | 2.0 | 38.2 | 0.33 | 95.2 | 89.4 | 6.1 |

In Table 1, samples in which * is attached to Sample No. are samples which do not satisfy the requirements of the present invention described above and samples in which * is not attached to Sample No. are samples which satisfy the requirements of the present invention described above.

<Measurement of Pore Distribution>

Figure 1:
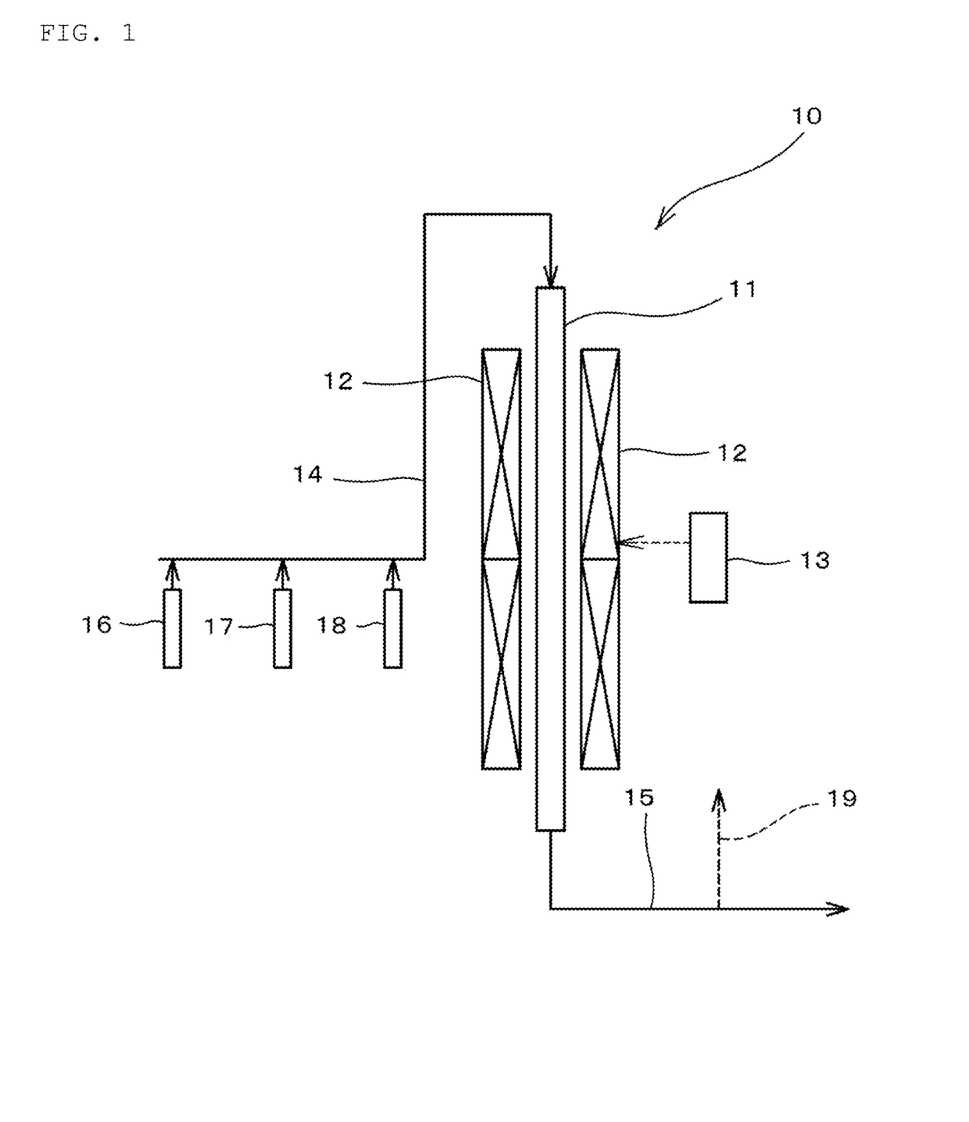
FIG. 1 is a diagram illustrating a schematic configuration of a testing apparatus used for a test to evaluate the organic substance decomposing performance of a catalyst for decomposing an organic substance.

The catalysts for organic substance decomposition of Sample Nos. 1 to 16 were each subjected to the pore distribution measurement by a mercury press-in method to determine the average pore diameter and the pore volume. The average pore diameter is the average value of the diameters, more specifically equivalent circle diameters of a plurality of pores. For the measurement, a measuring apparatus by mercury press-in method manufactured by Micromeritics was used. The pressure measuring method using this measuring apparatus by mercury press-in method is a storage type, and the press-in quantity measuring method is an electric capacitance type. The measurement conditions were set so that the mercury contact angle was (1) Testing Apparatus FIG. 1 is a diagram illustrating the schematic configuration of a testing apparatus 10 used for a test to evaluate the organic substance decomposing performance of a catalyst for decomposing an organic substance. This testing apparatus 10 includes a pipe 11 defining a flow path through which an organic substance flows, a heating unit 12 for heating the organic substance flowing through the pipe 11, and a control unit 13 which controls the heating unit 12.

A catalyst for decomposing an organic substance fabricated by the above-described method is disposed in a region to be heated by the heating unit 12 inside the pipe 11.

Figure 2:
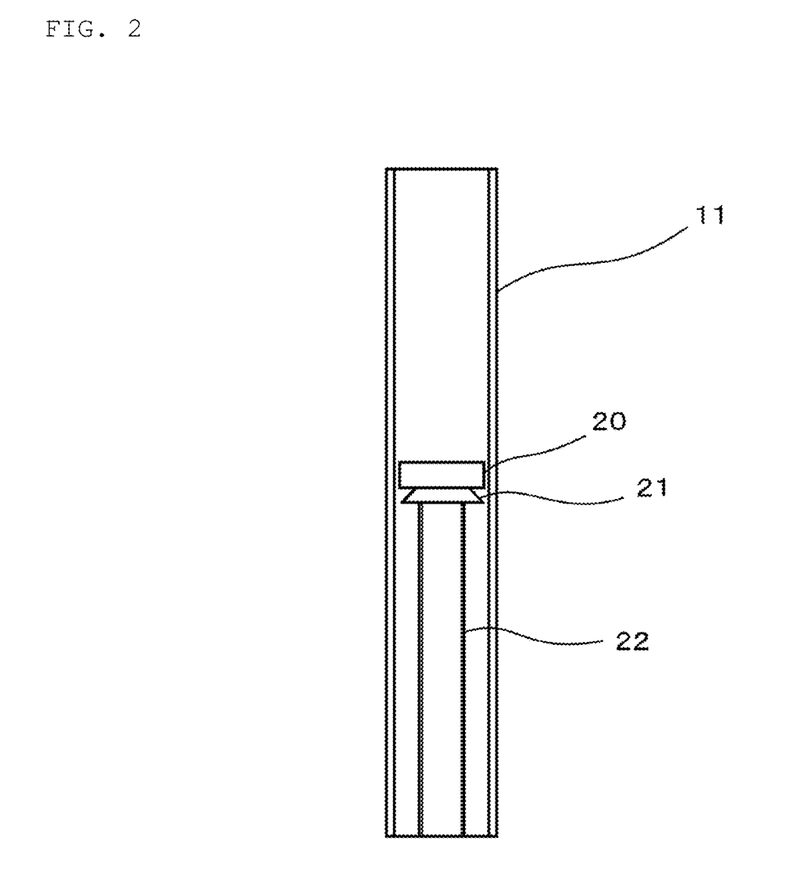
FIG. 2 is a sectional view for explaining a method for disposing a catalyst for decomposing an organic substance inside a pipe.

FIG. 2 is a sectional view for explaining the method for disposing a catalyst for decomposing an organic substance 20 inside the pipe 11. The catalyst for decomposing an organic substance 20, which had been classified into 0.5 mm to 0.6 mm particles with a mesh, was filled in the central portion of the ¼-inch sized pipe 11. The catalyst for decomposing an organic substance 20 is supported by a thermocouple 22 with a glass wool 21 interposed therebetween. The thermocouple 22 is provided to measure the temperature of the catalyst for decomposing an organic substance 20.

The gas to be treated which is supplied to the pipe 11 passes through the region in which the catalyst for decomposing an organic substance 20 is disposed and is discharged to a gas discharge pipe 15 to be described later.

As illustrated in FIG. 1, a gas supply pipe 14 is connected on the upstream side of the pipe 11. A toluene supply line 16 for supplying toluene that is an organic substance, a nitrogen supply line 17 for supplying nitrogen ($N_2$), and an oxygen supply line 18 for supplying oxygen ($O_2$) are connected to the gas supply pipe 14. In other words, the gas to be treated which contains toluene, nitrogen, and oxygen is supplied to the pipe 11 via the gas supply pipe 14.

The gas discharge pipe 15 for discharging the treated gas after being subjected to the decomposition of organic substance to the outside of the system is connected on the downstream side of the pipe 11. A sampling line 19 for sampling the treated gas is connected to the gas discharge pipe 15, and the testing apparatus is configured so that the concentration of toluene in the treated gas can be analyzed by gas chromatography.

The control unit 13 is configured so that the temperature of the region heated by the heating unit 12 can be controlled.

(2) Testing Method

Using the testing apparatus 10 described above, a test was conducted in which a gas to be treated which contained toluene, nitrogen, and oxygen was continuously supplied to the pipe 11 and toluene was decomposed. The composition of the gas to be treated was set to toluene ($C_7H_8$): 50 ppm, nitrogen ($N_2$): 80%, and oxygen ($O_2$): 20% as a volume concentration, the space velocity SV at the time of measurement was set to 150000/h, and the catalyst temperature was set to 300° C.

The treated gas was sampled at the outlet of the sampling line 19, and the toluene concentration was quantified through analysis by gas chromatography. The toluene decomposition rate was determined based on the following Equation (1). In Equation (1), "50" is the concentration of toluene contained in the gas to be treated before being subjected to the treatment.

$$\text{Toluene decomposition rate (\%)}=100-100\times(\text{toluene concentration}/50) \quad (1)$$

<Evaluation on Heat Resistance>

The catalysts for organic substance decomposition of Sample Nos. 1 to 16 were each subjected to a high temperature heat treatment to be heated at 1400° C. for 3 hours in an electric furnace. Thereafter, the toluene decomposition rate was determined under the above-mentioned conditions using the catalysts for organic substance decomposition after being subjected to the high temperature heat treatment.

The deterioration rate of the toluene decomposition rate by a high temperature heat treatment was calculated according to the following Equation (2), where C1 denoted the toluene decomposition rate in the case of using the catalyst for decomposing an organic substance before being subjected to the high temperature heat treatment and C2 denoted the toluene decomposition rate in the case of using the catalyst for decomposing an organic substance after being subjected to the high temperature heat treatment.

$$\text{Deterioration rate (\%)}=100-100\times(C2/C1) \quad (2)$$

The fact that "the organic substance decomposition rate after the catalyst for decomposing an organic substance is subjected to a heat treatment at 1400° C. for 3 hours is greater than 0.97 when the organic substance decomposition rate before the heat treatment is regarded as 1" is equivalent to the fact that the deterioration rate is smaller than 3%.

The composition of catalyst, firing temperature, average particle diameter D50 of catalyst particles, molding density of catalyst, average pore diameter, pore volume, toluene decomposition rate before high temperature heat treatment, toluene decomposition rate after high temperature heat treatment, and deterioration rate are presented in Table 1, respectively.

In the catalysts for organic substance decomposition of Sample Nos. 1 to 16 in Table 1, the A of the perovskite-type composite oxide represented by $A_xB_yM_zO_w$ is Ba, the B is Zr, the M is Mn, x is 1.010, y is 0.900, and z is 0.100.

The catalysts for decomposing an organic substance of Sample Nos. 2 to 15 are samples having different average pore diameters from one another within a range of 49 nm to 260 nm and different pore volumes from one another within a range of 0.08 cm$^3$/g to 0.37 cm$^3$/g and are samples which satisfy the requirements of the present invention. The deterioration rate was less than 3% in all of these catalysts.

In other words, even when the catalysts of Sample Nos. 2 to 15 satisfying the requirements of the present invention are exposed to a high temperature of 1400° C., a decrease in catalytic activity is sufficiently suppressed. This occurs because the effective surface area of the catalyst in contact with the gas to be treated containing an organic substance increases as the average pore diameter and the pore volume are optimized, and thus the catalytically active points increase. This is because the contact area between the catalyst particles is small and this suppresses the occurrence of sintering when the catalyst is used in a high temperature environment and a decrease in catalytically active points.

On the other hand, in the catalyst of Sample No. 1 which had an average pore diameter of 32.1 mm and thus did not satisfy the requirements of the present invention, the deterioration rate was 7.6% (i.e., greater than 3%). In the catalyst of Sample No. 16 which had an average pore diameter of 38.2 mm and thus did not satisfy the requirements of the present invention, the deterioration rate was 6.1% (i.e., greater than 3%).

Among the catalysts of Sample Nos. 2 to 15 which satisfied the requirements of the present invention, in the catalysts of Sample Nos. 2 to 6 and 8 to 15 having a pore volume of 0.10 cm$^3$/g or more, the toluene decomposition rates before and after the high temperature heat treatment were both 90% or more. Hence, it is more preferable that the catalyst for decomposing an organic substance which satisfies the requirements of the present invention has a pore volume of 0.10 cm$^3$/g or more.

Among the catalysts of Sample Nos. 2 to 15 which satisfied the requirements of the present invention, in the catalysts for organic substance decomposition of Sample Nos. 10 to 15 having an average pore diameter of 150 nm or more and a pore volume of 0.21 cm$^3$/g or more, the toluene decomposition rates before and after the high temperature heat treatment were both 90% or more and the deterioration rate was 0.6% or less. Hence, it is more preferable that the catalyst which satisfies the requirements of the present invention has an average pore diameter of 150 nm or more and a pore volume of 0.21 cm$^3$/g or more.

Example 2

Subsequently, the catalysts of Sample Nos. 17 to 28 presented in Table 2 were fabricated for the purpose of confirming the properties when the composition ratio of catalyst was changed. For these catalysts for decomposing an organic substance thus fabricated, the average pore diameter, pore volume, toluene decomposition rate before high temperature heat treatment, toluene decomposition rate after high temperature heat treatment, and deterioration rate were determined by similar methods to those in Example 1.

satisfying the requirements of the present invention are exposed to a high temperature of 1400° C., a decrease in catalytic activity is sufficiently suppressed.

On the other hand, in the catalyst of Sample No. 24 in which the composition z was out of the range of $0.05 \leq z \leq 0.2$

TABLE 2

| Sample No. | Charged composition ratio | | | | A(x) | | B(y) | M(z) | | | | Firing temperature | Average particle diameter D50 μm |
|---|---|---|---|---|---|---|---|---|---|---|---|---|---|
| | x | y | z | y + z | Ba | Sr | Zr | Mn | Co | Ni | Fe | | |
| 17* | 0.995 | 0.900 | 0.100 | 1.000 | 1.000 | | 1.000 | 1.000 | | | | 1050° C. | 0.842 |
| 18* | 1.000 | 0.900 | 0.100 | 1.000 | 1.000 | | 1.000 | 1.000 | | | | 1050° C. | 0.829 |
| 19 | 1.001 | 0.900 | 0.100 | 1.000 | 1.000 | | 1.000 | 1.000 | | | | 1050° C. | 0.803 |
| 20 | 1.005 | 0.900 | 0.100 | 1.000 | 1.000 | | 1.000 | 1.000 | | | | 1050° C. | 0.785 |
| 21 | 1.010 | 0.900 | 0.100 | 1.000 | 1.000 | | 1.000 | 1.000 | | | | 1050° C. | 0.780 |
| 22 | 1.050 | 0.900 | 0.100 | 1.000 | 1.000 | | 1.000 | 1.000 | | | | 1050° C. | 0.756 |
| 23 | 1.100 | 0.900 | 0.100 | 0.100 | 1.000 | | 1.000 | 1.000 | | | | 1050° C. | 0.732 |
| 24* | 1.010 | 0.600 | 0.400 | 1.000 | 1.000 | | 1.000 | 1.000 | | | | 1050° C. | 0.856 |
| 25 | 1.010 | 0.800 | 0.200 | 1.000 | 1.000 | | 1.000 | 1.000 | | | | 1050° C. | 0.814 |
| 26 | 1.010 | 0.950 | 0.050 | 1.000 | 1.000 | | 1.000 | 1.000 | | | | 1050° C. | 0.732 |
| 27 | 1.010 | 0.900 | 0.100 | 1.000 | 1.000 | | 1.000 | 1.000 | | | | 1050° C. | 0.780 |
| 28 | 1.010 | 0.850 | 0.150 | 1.000 | 1.000 | | 1.000 | 1.000 | | | | 1050° C. | 0.799 |

| Sample No. | Molding density g/cm³ | Average pore diameter nm | Pore volume cm³/g | Before high temperature heat treatment Decomposition rate % | After high temperature heat treatment Decomposition rate % | Deterioration rate % |
|---|---|---|---|---|---|---|
| 17* | 2.8 | 69.8 | 0.17 | 93.4 | 88.4 | 5.4 |
| 18* | 2.8 | 69.4 | 0.18 | 94.5 | 91.5 | 3.2 |
| 19 | 2.8 | 68.9 | 0.18 | 95.3 | 93.3 | 2.1 |
| 20 | 2.8 | 68.1 | 0.17 | 96.2 | 94.6 | 1.7 |
| 21 | 2.8 | 67.0 | 0.17 | 96.6 | 95.2 | 1.4 |
| 22 | 2.8 | 64.0 | 0.16 | 96.5 | 95.5 | 1.0 |
| 23 | 2.8 | 51.0 | 0.16 | 89.5 | 86.6 | 0.2 |
| 24* | 2.8 | 50.0 | 0.17 | 93.1 | 87.0 | 6.5 |
| 25 | 2.8 | 62.0 | 0.18 | 94.4 | 92.4 | 2.1 |
| 26 | 2.8 | 75.0 | 0.16 | 94.6 | 93.5 | 1.1 |
| 27 | 2.8 | 67.0 | 0.17 | 96.6 | 95.2 | 1.4 |
| 28 | 2.8 | 60.0 | 0.17 | 94.6 | 93.0 | 1.7 |

In Table 2, samples in which * is attached to Sample No. are samples which do not satisfy the requirements of the present invention described above and samples in which * is not attached to Sample No. are samples which satisfy the requirements of the present invention described above.

The catalysts of Sample Nos. 17 to 23 are samples in which the compositions y and z are the same as one another but the composition x is different from one another. The deterioration rate was less than 3.0% in all of the catalysts of Sample Nos. 19 to 23 satisfying the requirements of the present invention. In other words, even when the catalysts of Sample Nos. 19 to 23 satisfying the requirements of the present invention are exposed to a high temperature of 1400° C., a decrease in catalytic activity is sufficiently suppressed.

On the other hand, in the catalysts of Sample Nos. 17 and 18 in which the composition x was out of the range of $1.001 \leq x \leq 1.1$ and the requirements of the present invention were not satisfied, the deterioration rates were 5.4% and 3.2%, respectively (i.e., greater than 3.0%).

The catalysts of Sample Nos. 24 to 28 are samples in which the composition x is 1.010 and the compositions y and z are different from one another. The deterioration rate was less than 3.0% in the catalysts of Sample Nos. 25 to 28 satisfying the requirements of the present invention. In other words, even when the catalysts of Sample Nos. 25 to 28 and which did not satisfy the requirements of the present invention, the deterioration rate was 6.5 (i.e., greater than 3.0%).

Among the catalysts of Sample Nos. 19 to 23 and 25 to 28 which satisfied the requirements of the present invention, in the catalysts of Sample Nos. 19 to 22 and 25 to 28 in which the composition x satisfied the relation of $x \leq 1.05$, the toluene decomposition rates before and after the high temperature heat treatment were both 90% or more. Hence, in the catalyst for decomposing an organic substance which satisfies the requirements of the present invention, it is more preferable that the composition x satisfies the relation of $x \leq 1.05$.

Example 3

Subsequently, the catalysts of Sample Nos. 29 to 48 presented in Table 3 were fabricated for the purpose of confirming the properties when the composition of the catalyst was changed. Here, in addition to the raw material powders used when fabricating the catalysts of Sample Nos. 1 to 16 in Table 1, high-purity $SrCO_3$ powder, $Co_3O_4$ powder, NiO powder, and $Fe_2O_3$ powder were prepared, and perovskite-type composite oxides were fabricated so as to have the compositions presented in Table 3.

An additive and water were added to the obtained perovskite-type composite oxide, and the mixture was wet-mixed together with $ZrO_2$ cobble stones to obtain a slurry. This slurry was dried at 120° C. in a dryer and then molded using a press molding machine so as to be a cylindrical pellet having a molding density of 2.8 g/cm³, a diameter of 8 mm, and a length of 8 mm. The molded body obtained was fired at 1050° C. for 2 hours, and the fired product obtained was pulverized using a mortar and classified to obtain a 0.5 mm to 0.6 mm particulate catalyst for decomposing an organic substance.

For the catalysts for decomposing an organic substance thus fabricated, the average pore diameter, pore volume, toluene decomposition rate before additional heat treatment, toluene decomposition rate after additional heat treatment, and deterioration rate were determined by similar methods to those in Example 1.

In Table 3, samples in which * is attached to Sample No. are samples which do not satisfy the requirements of the present invention described above and samples in which * is not attached to Sample No. are samples which satisfy the requirements of the present invention described above.

The catalysts of Sample Nos. 29 to 33 are samples in which the A of the perovskite-type composite oxide represented by $A_xB_yM_zO_w$ is Ba, the B is Zr, and the M is Co. The deterioration rate was less than 3.0% in the catalysts of Sample Nos. 30 to 32 satisfying the requirements of the present invention. In other words, even when the catalysts of Sample Nos. 30 to 32 satisfying the requirements of the present invention are exposed to a high temperature of 1400° C., a decrease in catalytic activity is sufficiently suppressed.

On the other hand, in the catalyst of Sample No. 29 in which the composition x was out of the range of $1.001 \leq x \leq 1.1$ and the catalyst of Sample No. 33 in which the

TABLE 3

| Sample No. | Charged composition ratio | | | | A(x) | | B(y) | M(z) | | | |
|---|---|---|---|---|---|---|---|---|---|---|---|
| | x | y | z | y + z | Ba | Sr | Zr | Mn | Co | Ni | Fe |
| 29* | 1.000 | 0.900 | 0.100 | 1.000 | 1.000 | | 1.000 | | 1.000 | | |
| 30 | 1.001 | 0.900 | 0.100 | 1.000 | 1.000 | | 1.000 | | 1.000 | | |
| 31 | 1.005 | 0.900 | 0.100 | 1.000 | 1.000 | | 1.000 | | 1.000 | | |
| 32 | 1.005 | 0.800 | 0.200 | 1.000 | 1.000 | | 1.000 | | 1.000 | | |
| 33* | 1.005 | 0.600 | 0.400 | 1.000 | 1.000 | | 1.000 | | 1.000 | | |
| 34* | 1.000 | 0.900 | 0.100 | 1.000 | 1.000 | | 1.000 | 0.400 | 0.400 | 0.100 | 0.100 |
| 35 | 1.001 | 0.900 | 0.100 | 1.000 | 1.000 | | 1.000 | 0.400 | 0.400 | 0.100 | 0.100 |
| 36 | 1.005 | 0.900 | 0.100 | 1.000 | 1.000 | | 1.000 | 0.400 | 0.400 | 0.100 | 0.100 |
| 37 | 1.005 | 0.800 | 0.200 | 1.000 | 1.000 | | 1.000 | 0.400 | 0.400 | 0.100 | 0.100 |
| 38* | 1.005 | 0.600 | 0.400 | 1.000 | 1.000 | | 1.000 | 0.400 | 0.400 | 0.100 | 0.100 |
| 39* | 1.000 | 0.900 | 0.100 | 1.000 | | 1.000 | 1.000 | | 1.000 | | |
| 40 | 1.001 | 0.900 | 0.100 | 1.000 | | 1.000 | 1.000 | | 1.000 | | |
| 41 | 1.005 | 0.900 | 0.100 | 1.000 | | 1.000 | 1.000 | | 1.000 | | |
| 42 | 1.005 | 0.800 | 0.200 | 1.000 | | 1.000 | 1.000 | | 1.000 | | |
| 43* | 1.005 | 0.600 | 0.400 | 1.000 | | 1.000 | 1.000 | | 1.000 | | |
| 44* | 1.000 | 0.900 | 0.100 | 1.000 | 0.500 | 0.500 | 1.000 | 0.700 | 0.200 | 0.050 | 0.050 |
| 45 | 1.001 | 0.900 | 0.100 | 1.000 | 0.500 | 0.500 | 1.000 | 0.700 | 0.200 | 0.050 | 0.050 |
| 46 | 1.005 | 0.900 | 0.100 | 1.000 | 0.500 | 0.500 | 1.000 | 0.700 | 0.200 | 0.050 | 0.050 |
| 47 | 1.005 | 0.800 | 0.200 | 1.000 | 0.500 | 0.500 | 1.000 | 0.700 | 0.200 | 0.050 | 0.050 |
| 48* | 1.005 | 0.600 | 0.400 | 1.000 | 0.500 | 0.500 | 1.000 | 0.700 | 0.200 | 0.050 | 0.050 |

| Sample No. | Average pore diameter nm | Pore volume cm³/g | Before high temperature heat treatment Decomposition rate % | After high temperature heat treatment Decomposition rate % | Deterioration rate % |
|---|---|---|---|---|---|
| 29* | — | — | 92.8 | 83.1 | 10.4 |
| 30 | — | — | 93.1 | 90.7 | 2.6 |
| 31 | 69.10 | 0.26 | 93.6 | 92.5 | 1.2 |
| 32 | | | 95.0 | 93.0 | 2.1 |
| 33* | | | 94.8 | 82.4 | 13.1 |
| 34* | — | — | 91.1 | 80.4 | 11.7 |
| 35 | — | — | 91.6 | 88.9 | 2.9 |
| 36 | 70.98 | 0.36 | 92.4 | 90.8 | 1.7 |
| 37 | — | — | 93.6 | 91.4 | 2.3 |
| 38* | — | — | 93.0 | 78.6 | 15.5 |
| 39* | — | — | 87.1 | 76.6 | 12.1 |
| 40 | — | — | 87.6 | 85.1 | 2.8 |
| 41 | 55.54 | 0.18 | 88.6 | 87.3 | 1.5 |
| 42 | — | — | 92.0 | 90.0 | 2.2 |
| 43* | — | — | 90.1 | 76.1 | 15.5 |
| 44* | — | — | 91.4 | 81.3 | 11.0 |
| 45 | — | — | 91.9 | 89.2 | 2.9 |
| 46 | 59.97 | 0.19 | 93.2 | 91.7 | 1.6 |
| 47 | — | — | 94.9 | 92.8 | 2.2 |
| 48* | — | | 93.6 | 80.2 | 14.3 | composition z was out of the range of 0.05≤z≤0.2, the deterioration rates were 10.4% and 13.1%, respectively (i.e., greater than 3%).

The average pore diameter and pore volume of only the catalyst of Sample No. 31 are determined since the catalysts of Sample Nos. 29 to 33 have approximately the same average pore diameter and pore volume as one another.

The catalysts of Sample Nos. 34 to 38 are samples in which the A of the perovskite-type composite oxide represented by $A_xB_yM_zO_w$ is Ba, the B is Zr, and the M is Mn, Co, Ni, and Fe. The deterioration rate was less than 3.0% in the catalysts of Sample Nos. 35 to 37 satisfying the requirements of the present invention. In other words, even when the catalysts of Sample Nos. 35 to 37 satisfying the requirements of the present invention are exposed to a high temperature of 1400° C., a decrease in catalytic activity is sufficiently suppressed.

On the other hand, in the catalyst of Sample No. 34 in which the composition x was out of the range of 1.001≤x≤1.1 and the catalyst of Sample No. 38 in which the composition z was out of the range of 0.05≤z≤0.2, the deterioration rates were 11.7% and 15.5%, respectively (i.e., greater than 3%).

The average pore diameter and pore volume of only the catalyst of Sample No. 36 are determined since the catalysts of Sample Nos. 34 to 38 have approximately the same average pore diameter and pore volume as one another.

The catalysts of Sample Nos. 39 to 43 are samples in which the A of the perovskite-type composite oxide represented by $A_xB_yM_zO_w$ is Sr, the B is Zr, and the M is Mn. The deterioration rate was less than 3.0% in the catalysts of Sample Nos. 40 to 42 satisfying the requirements of the present invention. In other words, even when the catalysts of Sample Nos. 40 to 42 satisfying the requirements of the present invention are exposed to a high temperature of 1400° C., a decrease in catalytic activity is sufficiently suppressed.

On the other hand, in the catalyst of Sample No. 39 in which the composition x was out of the range of 1.001≤x≤1.1 and the catalyst of Sample No. 43 in which the composition z was out of the range of 0.05≤z≤0.2, the deterioration rates were 12.1% and 15.5%, respectively (i.e., greater than 3%).

The average pore diameter and pore volume of only the catalyst of Sample No. 41 are determined since the catalysts of Sample Nos. 39 to 43 have approximately the same average pore diameter and pore volume as one another.

The catalysts of Sample Nos. 44 to 48 are samples in which the A of the perovskite-type composite oxide represented by $A_xB_yM_zO_w$ is Ba and Sr, the B is Zr, and the M is Mn, Co, Ni, and Fe. The deterioration rate was less than 3.0% in the catalysts of Sample Nos. 45 to 47 satisfying the requirements of the present invention. In other words, even when the catalysts of Sample Nos. 45 to 47 satisfying the requirements of the present invention are exposed to a high temperature of 1400° C., a decrease in catalytic activity is sufficiently suppressed.

On the other hand, in the catalyst of Sample No. 44 in which the composition x was out of the range of 1.001≤x≤1.1 and the catalyst of Sample No. 48 in which the composition z was out of the range of 0.05≤z≤0.2, the deterioration rates were 11.0% and 14.3%, respectively (i.e., greater than 3%).

The average pore diameter and pore volume of only the catalyst of Sample No. 46 are determined since the catalysts of Sample Nos. 44 to 48 have approximately the same average pore diameter and pore volume as one another.

The present invention is not limited to the embodiments, and various applications and modifications can be added within the scope of the present invention.

In the above description, an example in which toluene is decomposed using the catalyst for decomposing an organic substance of the present invention has been described, but the organic substance is not limited to toluene.

In Examples described above, the average pore diameter and pore volume of the catalyst for decomposing an organic substance were adjusted by adjusting the firing temperature when fabricating the catalyst for decomposing an organic substance, the average particle diameter D50 of the perovskite-type composite oxide, and the molding density, but the method for adjusting the average pore diameter and pore volume is not limited to the methods described above.

In Examples described above, the experimental results are presented that the deterioration rate is less than 3% when M of the perovskite-type composite oxide represented by $A_xB_yM_zO_w$ is Mn, when M is Co, and when M is Mn, Co, Ni, and Fe. However, M is only required to be at least one selected from the group consisting of Mn, Co, Ni, and Fe, and the deterioration rate is less than 3% in that case.

DESCRIPTION OF REFERENCE SYMBOLS

10: Testing apparatus
11: Pipe
12: Heating unit
13: Control unit
14: Gas supply pipe
15: Gas discharge pipe
16: Toluene supply line
17: Nitrogen supply line
18: Oxygen supply line
19: Sampling line

The invention claimed is:

1. A catalyst for decomposing an organic substance, the catalyst comprising a body having a plurality of pores, the body containing a perovskite composite oxide represented by $A_xB_yM_zO_w$, where
the A is at least one selected from Ba and Sr,
the B is Zr,
the M is at least one selected from Mn, Co, Ni, and Fe,
1.001≤x≤1.1,
0.05≤z≤0.2,
y+z=1,
w is a positive value that satisfies electrical neutrality, and
an average pore diameter of the plurality of pores is 49 nm to 260 nm and a pore volume of each of the plurality of pores is 0.08 cm³/g to 0.37 cm³/g.

2. The catalyst for decomposing an organic substance according to claim 1, wherein an organic substance decomposition rate after the catalyst is subjected to a heat treatment at 1400° C. for 3 hours is greater than 0.97 when the organic substance decomposition rate before the heat treatment is regarded as 1.

3. The catalyst for decomposing an organic substance according to claim 1, wherein 1.001≤x≤1.05.

4. The catalyst for decomposing an organic substance according to claim 1, wherein the pore volume is 0.10 cm³/g to 0.37 cm³/g.

5. The catalyst for decomposing an organic substance according to claim 1, wherein the average pore diameter is 150 nm to 260 nm, and the pore volume is 0.21 cm³/g to 0.37 cm³/g.

6. An organic substance decomposing apparatus comprising a flow path for an organic substance, and the catalyst for decomposing an organic substance according to claim 1 within the flow path.

7. The organic substance decomposing apparatus according to claim 6, wherein an organic substance decomposition rate of the catalyst after the catalyst is subjected to a heat treatment at 1400° C. for 3 hours is greater than 0.97 when the organic substance decomposition rate before the heat treatment is regarded as 1.

8. The organic substance decomposing apparatus according to claim 6, wherein $1.001 \leq x \leq 1.05$.

9. The organic substance decomposing apparatus according to claim 6, wherein the pore volume is $0.10$ cm$^3$/g to $0.37$ cm$^3$/g.

10. The organic substance decomposing apparatus according to claim 6, wherein the average pore diameter is 150 nm to 260 nm and the pore volume is $0.21$ cm$^3$/g to $0.37$ cm$^3$/g.

\* \* \* \* \*